US009878464B1

(12) United States Patent
Stark et al.

(10) Patent No.: US 9,878,464 B1
(45) Date of Patent: Jan. 30, 2018

(54) PRESERVATION OF CELLULOSIC MATERIALS, COMPOSITIONS AND METHODS THEREOF

(75) Inventors: Joseph L. Stark, Minneapolis, MN (US); Forrest S. Schultz, Menomonie, WI (US)

(73) Assignee: Apinee, Inc., Roseville, MN (US)

( * ) Notice: Subject to any disclaimer, the term of this patent is extended or adjusted under 35 U.S.C. 154(b) by 338 days.

(21) Appl. No.: 13/538,739

(22) Filed: Jun. 29, 2012

Related U.S. Application Data

(60) Provisional application No. 61/503,091, filed on Jun. 30, 2011.

(51) Int. Cl.
  *B05D 7/06* (2006.01)
  *B27K 3/15* (2006.01)
(52) U.S. Cl.
  CPC ..................................... *B27K 3/15* (2013.01)
(58) Field of Classification Search
  CPC ............................................................ B05D 7/06
  USPC ................................................. 427/384, 408
  See application file for complete search history.

(56) References Cited

U.S. PATENT DOCUMENTS

| | | |
|---|---|---|
| 2,006,207 A | 6/1935 | Bhagwat |
| 2,079,626 A | 5/1937 | Ashby et al. |
| 2,503,711 A * | 4/1950 | Bullard et al. ......... D03D 49/38 139/157 |
| 2,545,603 A * | 3/1951 | Byers ....................... B27D 1/00 156/255 |
| 2,717,423 A | 9/1955 | Murray, Jr. et al. |
| 2,962,459 A | 11/1960 | Ash et al. |
| 3,006,784 A | 10/1961 | Ryan et al. |
| 3,083,170 A | 3/1963 | Booty |
| 3,196,494 A | 7/1965 | Hoffmann et al. |
| 3,215,596 A | 11/1965 | Johnson et al. |
| 3,219,473 A | 11/1965 | Dimond |
| 3,322,318 A | 5/1967 | Turner et al. |
| 3,356,622 A | 12/1967 | Delmonte |
| 3,462,237 A | 8/1969 | Sellet |
| 3,468,822 A | 9/1969 | Wismer et al. |
| 3,491,067 A | 1/1970 | Sellet |
| 3,559,920 A | 2/1971 | Moore |
| 3,627,719 A | 12/1971 | Sellet |
| 3,644,171 A | 2/1972 | Bevan et al. |
| 3,674,415 A | 7/1972 | Sellet |
| 3,698,931 A | 10/1972 | Horowitz |
| 3,705,777 A | 12/1972 | Witkowski |
| 3,706,619 A | 12/1972 | Freeman |
| 3,713,879 A | 1/1973 | Wu |
| 3,737,488 A | 6/1973 | Porter et al. |
| 3,740,337 A | 6/1973 | Sommers |
| 3,847,857 A | 11/1974 | Haag et al. |
| 3,906,127 A | 9/1975 | Hollmann et al. |
| 3,915,919 A | 10/1975 | Nishioka et al. |
| 3,935,341 A | 1/1976 | Sorensen et al. |
| 3,935,467 A | 1/1976 | Gablin |
| 3,950,218 A | 4/1976 | Levesque |
| 3,964,385 A | 6/1976 | Knight |
| 3,965,047 A | 6/1976 | Yamaguchi |
| 3,993,721 A | 11/1976 | Soda et al. |
| 4,010,163 A | 3/1977 | Hesse et al. |
| 4,018,642 A | 4/1977 | Pike et al. |
| 4,026,847 A | 5/1977 | Ripa et al. |
| 4,040,823 A | 8/1977 | Yamaguchi |
| 4,048,101 A | 9/1977 | Nakamachi et al. |
| 4,081,414 A | 3/1978 | Abe et al. |
| 4,104,357 A | 8/1978 | Blair |
| 4,114,333 A | 9/1978 | Jones et al. |
| 4,115,178 A | 9/1978 | Cone et al. |
| 4,128,689 A | 12/1978 | Heaps et al. |
| 4,129,533 A | 12/1978 | Moore, Jr. |
| 4,141,944 A | 2/1979 | Anstadt et al. |
| 4,195,880 A | 4/1980 | Henkhaus |
| 4,230,600 A | 10/1980 | Bornstein |
| 4,230,822 A | 10/1980 | Murch et al. |
| 4,234,326 A | 11/1980 | Bailey et al. |
| 4,237,182 A | 12/1980 | Fulmer et al. |
| 4,244,901 A | 1/1981 | Wencley et al. |
| 4,252,857 A | 2/1981 | Heine et al. |
| 4,258,088 A | 3/1981 | Cone et al. |

(Continued)

FOREIGN PATENT DOCUMENTS

| | | |
|---|---|---|
| CA | 1 125 764 | 6/1982 |
| CA | 1 141 099 | 2/1983 |

(Continued)

OTHER PUBLICATIONS

Matsumoto et al., Viscosity-Molecular Weight Relationship for Polyvinyl Acetate, 1960, Journal of polymer science, vol. XLVI, pp. 441-451).*
Derwent of DE10233179A1, 2004.*
U.S. Appl. No. 61/141,920 specification.*
U.S. Appl. No. 61/141,920 claim.*
Cooke, T.F., American Cyanamid Company, Bound Brook, NJ, *Resistance to Microbiological Deterioration of Resin-Treated Cellulosic Fabrics*, Textile Research Journal, vol. 24(3):197, 13 pages, Sage Publications, Inc., Mar. 1, 1954.

(Continued)

*Primary Examiner* — Dah-Wei D Yuan
*Assistant Examiner* — Hai Yan Zhang
(74) *Attorney, Agent, or Firm* — Merchant & Gould P.C.

(57) ABSTRACT

The disclosure relates to compositions for preservation of cellulosic materials and methods of applying compositions for preservation of cellulosic materials. The compositions comprise a pre-polymer and optional nonionic surfactants and other additives. Compositions of optional nonionic surfactant mixtures and pre-polymers can be used advantageously in methods to preserve cellulosic materials by application of the material with preservatives at ambient atmospheric pressures.

13 Claims, No Drawings

(56) References Cited

U.S. PATENT DOCUMENTS

| | | | | |
|---|---|---|---|---|
| 4,264,760 A | * | 4/1981 | Meyer | C08K 3/30 525/505 |
| 4,265,963 A | | 5/1981 | Matalon | |
| 4,301,215 A | * | 11/1981 | Deubzer | B27K 3/15 427/297 |
| 4,357,377 A | | 11/1982 | Yamamoto | |
| 4,374,687 A | | 2/1983 | Yamamoto | |
| 4,382,884 A | | 5/1983 | Berini et al. | |
| 4,403,013 A | | 9/1983 | Robitschek et al. | |
| 4,425,998 A | | 1/1984 | Hof et al. | |
| 4,430,468 A | | 2/1984 | Schumacher | |
| 4,433,120 A | | 2/1984 | Chiu | |
| 4,439,070 A | | 3/1984 | Dimmick | |
| 4,443,520 A | | 4/1984 | Braithwaite, Jr. | |
| 4,515,739 A | | 5/1985 | Maine | |
| 4,545,597 A | | 10/1985 | Meatto et al. | |
| 4,559,162 A | | 12/1985 | Abel et al. | |
| 4,582,758 A | | 4/1986 | Bruce et al. | |
| 4,595,710 A | | 6/1986 | Albertelli et al. | |
| 4,609,690 A | | 9/1986 | Gruber et al. | |
| 4,649,793 A | | 3/1987 | Blackshear et al. | |
| 4,652,393 A | | 3/1987 | Ely et al. | |
| 4,661,382 A | * | 4/1987 | Cooke, Jr. | B27K 3/166 106/18.32 |
| 4,714,577 A | | 12/1987 | Nagamoto et al. | |
| 4,743,633 A | | 5/1988 | Navratil et al. | |
| 4,777,987 A | | 10/1988 | Asagi et al. | |
| 4,780,988 A | | 11/1988 | Mielke et al. | |
| 4,810,741 A | | 3/1989 | Kim | |
| 4,818,590 A | | 4/1989 | Prince et al. | |
| 4,852,314 A | | 8/1989 | Moore, Jr. | |
| 4,871,594 A | | 10/1989 | Bister et al. | |
| 4,992,481 A | | 2/1991 | von Bonin et al. | |
| 5,021,122 A | | 6/1991 | Desrochers et al. | |
| 5,026,530 A | | 6/1991 | Drinkard, Jr. et al. | |
| 5,055,410 A | | 10/1991 | Blumenthal et al. | |
| 5,060,291 A | | 10/1991 | Albertelli | |
| 5,074,946 A | | 12/1991 | Daisy | |
| 5,075,052 A | | 12/1991 | Malvassora | |
| 5,086,084 A | | 2/1992 | Michaelson | |
| 5,091,240 A | | 2/1992 | Kajander et al. | |
| 5,115,609 A | | 5/1992 | Sing | |
| 5,135,612 A | | 8/1992 | Desrochers et al. | |
| 5,139,861 A | | 8/1992 | Williams et al. | |
| 5,162,394 A | | 11/1992 | Trocino et al. | |
| 5,202,150 A | | 4/1993 | Benson et al. | |
| 5,218,793 A | | 6/1993 | Ball | |
| 5,245,812 A | | 9/1993 | Landers | |
| 5,247,005 A | | 9/1993 | von Bonin et al. | |
| 5,290,602 A | | 3/1994 | Argyropoulos et al. | |
| 5,296,176 A | | 3/1994 | Nakamura | |
| 5,299,400 A | | 4/1994 | Sing | |
| 5,303,720 A | | 4/1994 | Banerjee et al. | |
| 5,318,844 A | | 6/1994 | Brandon | |
| 5,320,891 A | | 6/1994 | Levy et al. | |
| 5,342,629 A | * | 8/1994 | Brown | A01N 59/04 424/601 |
| 5,344,493 A | | 9/1994 | Jackson | |
| 5,351,847 A | | 10/1994 | Greenbaum | |
| 5,362,519 A | | 11/1994 | Argyropoulos et al. | |
| 5,368,794 A | | 11/1994 | Ou | |
| 5,401,793 A | | 3/1995 | Kobayashi et al. | |
| 5,409,777 A | | 4/1995 | Kennedy et al. | |
| 5,416,140 A | | 5/1995 | Columbus et al. | |
| 5,418,282 A | | 5/1995 | Wiehn | |
| 5,421,922 A | | 6/1995 | Sperber | |
| 5,434,200 A | | 7/1995 | Kolker et al. | |
| 5,442,023 A | | 8/1995 | Argyropoulos et al. | |
| 5,462,589 A | | 10/1995 | Nicholas et al. | |
| 5,469,691 A | | 11/1995 | Grey et al. | |
| 5,470,924 A | | 11/1995 | Ryan | |
| 5,498,761 A | | 3/1996 | Wessling et al. | |
| 5,502,088 A | | 3/1996 | Hododi | |
| 5,507,985 A | | 4/1996 | Cadorniga | |
| 5,515,792 A | | 5/1996 | Bullock et al. | |
| 5,549,869 A | | 8/1996 | Iwakawa | |
| 5,554,429 A | | 9/1996 | Iwata et al. | |
| 5,582,670 A | | 12/1996 | Andersen et al. | |
| 5,612,111 A | | 3/1997 | Lin | |
| 5,616,419 A | | 4/1997 | Hsu et al. | |
| 5,635,248 A | | 6/1997 | Hsu et al. | |
| 5,639,800 A | | 6/1997 | von Bonin et al. | |
| 5,676,905 A | | 10/1997 | Andersen et al. | |
| 5,715,887 A | | 2/1998 | Hosokawa | |
| 5,733,633 A | | 3/1998 | Lin | |
| 5,736,218 A | | 4/1998 | Iwata et al. | |
| 5,766,525 A | | 6/1998 | Andersen et al. | |
| 5,769,735 A | | 6/1998 | Hosokawa | |
| 5,783,543 A | | 7/1998 | Fleckenstein et al. | |
| 5,786,072 A | | 7/1998 | Hsu et al. | |
| 5,800,647 A | | 9/1998 | Andersen et al. | |
| 5,804,641 A | | 9/1998 | Iwakawa | |
| 5,820,737 A | | 10/1998 | Kohn | |
| 5,830,548 A | | 11/1998 | Andersen et al. | |
| 5,843,329 A | | 12/1998 | Deetz | |
| 5,902,597 A | | 5/1999 | Iwakawa et al. | |
| 5,910,275 A | | 6/1999 | Hausdorf et al. | |
| 5,922,379 A | | 7/1999 | Wang | |
| 5,932,299 A | | 8/1999 | Katoot | |
| 5,935,675 A | | 8/1999 | Hayden et al. | |
| 5,945,213 A | | 8/1999 | Nagaike et al. | |
| 5,968,630 A | | 10/1999 | Foster | |
| 5,989,781 A | | 11/1999 | Idacavage et al. | |
| 5,990,224 A | | 11/1999 | Raynolds et al. | |
| 6,024,784 A | | 2/2000 | Buisman et al. | |
| 6,030,673 A | | 2/2000 | Andersen et al. | |
| 6,040,057 A | | 3/2000 | Slimak et al. | |
| 6,048,431 A | | 4/2000 | Clements et al. | |
| 6,066,680 A | | 5/2000 | Cope | |
| 6,083,601 A | | 7/2000 | Prince et al. | |
| 6,090,479 A | | 7/2000 | Shirato et al. | |
| 6,099,850 A | | 8/2000 | Voris et al. | |
| 6,130,268 A | | 10/2000 | Murray | |
| 6,171,688 B1 | | 1/2001 | Zheng et al. | |
| 6,180,037 B1 | | 1/2001 | Andersen et al. | |
| 6,184,285 B1 | | 2/2001 | Hatfield et al. | |
| 6,240,697 B1 | | 6/2001 | Thompson et al. | |
| 6,242,041 B1 | | 6/2001 | Katoot et al. | |
| 6,258,298 B1 | | 7/2001 | Blount | |
| 6,271,305 B1 | | 8/2001 | Rajalingam et al. | |
| 6,287,708 B1 | | 9/2001 | Viikari et al. | |
| 6,290,992 B1 | | 9/2001 | Magnuson-Hawkins | |
| 6,316,016 B1 | | 11/2001 | Iwakawa | |
| 6,319,511 B1 | | 11/2001 | Van Voris et al. | |
| 6,322,853 B1 | | 11/2001 | B | |
| 6,342,172 B1 | | 1/2002 | Finley | |
| 6,348,168 B1 | | 2/2002 | Lowrance et al. | |
| 6,355,193 B1 | | 3/2002 | Stott | |
| 6,368,544 B1 | | 4/2002 | Owens | |
| 6,369,171 B2 | | 4/2002 | Dupre et al. | |
| 6,383,996 B1 | | 5/2002 | Maurin et al. | |
| 6,395,824 B1 | | 5/2002 | Beutler et al. | |
| 6,401,414 B1 | | 6/2002 | Steel et al. | |
| 6,410,766 B2 | | 6/2002 | Roll et al. | |
| 6,412,245 B1 | | 7/2002 | Lane et al. | |
| 6,417,261 B1 | | 7/2002 | Maier et al. | |
| 6,432,254 B1 | * | 8/2002 | Black | B27N 3/002 156/307.5 |
| 6,442,912 B1 | | 9/2002 | Phillips et al. | |
| 6,455,606 B1 | | 9/2002 | Kaku et al. | |
| 6,461,472 B2 | | 10/2002 | Fujii | |
| 6,489,392 B1 | | 12/2002 | Lappalainen et al. | |
| 6,491,850 B1 | | 12/2002 | Blount | |
| 6,494,438 B1 | | 12/2002 | Noirot et al. | |
| 6,497,956 B1 | | 12/2002 | Phillips et al. | |
| 6,528,114 B1 | | 3/2003 | Summons | |
| 6,534,306 B1 | | 3/2003 | Allen | |
| 6,538,065 B1 | | 3/2003 | Suriano et al. | |
| 6,545,729 B1 | | 4/2003 | Lowe | |
| 6,548,609 B2 | | 4/2003 | Ramirez-De-Arellano-Aburto et al. | |
| 6,551,537 B2 | | 4/2003 | Chen | |
| 6,552,109 B1 | | 4/2003 | Chen | |
| 6,559,270 B1 | | 5/2003 | Siclovan et al. | |

(56) References Cited

U.S. PATENT DOCUMENTS

| | | |
|---|---|---|
| 6,562,410 B1 | 5/2003 | Mayer et al. |
| 6,572,956 B1 | 6/2003 | Picket et al. |
| 6,590,004 B1 | 7/2003 | Zehner |
| 6,598,700 B1 | 7/2003 | Schroeder |
| 6,607,739 B1 | 8/2003 | Wallo |
| 6,610,409 B2 | 8/2003 | Pickett et al. |
| 6,683,143 B1 | 1/2004 | Mumick et al. |
| 6,686,330 B2 | 2/2004 | Jordan, IV et al. |
| 6,691,485 B1 | 2/2004 | Prokofyev |
| 6,713,156 B1 | 3/2004 | Pauls et al. |
| 6,753,066 B2 | 6/2004 | Eby et al. |
| 6,759,444 B2 | 7/2004 | Brandoli et al. |
| 6,761,177 B1 | 7/2004 | Kedem-Shabi et al. |
| 6,800,352 B1 | 10/2004 | Hejna et al. |
| 6,822,135 B2 | 11/2004 | Soerens et al. |
| 6,844,071 B1 | 1/2005 | Wang et al. |
| 6,846,849 B2 | 1/2005 | Capps |
| 6,863,972 B2 | 3/2005 | Burger et al. |
| 6,868,643 B1 | 3/2005 | Williams |
| 6,890,965 B1 | 5/2005 | Johnson et al. |
| 6,908,677 B2 | 6/2005 | Shoshany et al. |
| 6,911,070 B2 | 6/2005 | Gang |
| 6,936,200 B2 | 8/2005 | Park et al. |
| 6,958,185 B1 | 10/2005 | Zehner |
| 6,962,754 B2 | 11/2005 | Bussi et al. |
| 6,972,277 B2 | 12/2005 | Dietz |
| 7,014,802 B1 | 3/2006 | Eby et al. |
| 7,029,516 B2 | 4/2006 | Campbell et al. |
| 7,063,895 B2 | 6/2006 | Rodrigues et al. |
| 7,097,879 B2 | 8/2006 | Bolton et al. |
| 7,112,626 B1 | 9/2006 | Fickeisen et al. |
| 7,132,023 B2 | 11/2006 | Virtanen et al. |
| 7,141,118 B2 | 11/2006 | Vaerewyck et al. |
| 7,141,195 B2 | 11/2006 | Winterowd et al. |
| 7,153,576 B2 | 12/2006 | Wang et al. |
| 7,160,841 B2 | 1/2007 | Fujita et al. |
| 7,211,318 B2 | 5/2007 | Lee et al. |
| 7,303,642 B2 | 12/2007 | Topolkaraev |
| 7,364,795 B2 | 4/2008 | Daly et al. |
| 7,371,787 B2 | 5/2008 | Preston et al. |
| 7,410,700 B2 | 8/2008 | Wang |
| 7,414,535 B2 | 8/2008 | Hanabusa et al. |
| 7,431,872 B2 | 10/2008 | Dostal et al. |
| 7,473,457 B2 | 1/2009 | Han et al. |
| 7,553,100 B2 | 6/2009 | Muhr-Sweeney |
| 7,595,365 B2 | 9/2009 | Kappes et al. |
| 7,712,265 B2 | 5/2010 | Overmyer, Jr. et al. |
| 7,770,342 B2 | 8/2010 | Marschke |
| 7,790,076 B2 | 9/2010 | Seiter et al. |
| 8,003,082 B2 | 8/2011 | Chaudhuri |
| 8,062,394 B2 | 11/2011 | Gaeta et al. |
| 8,153,261 B2 | 4/2012 | Landon et al. |
| 8,258,066 B2 | 9/2012 | Michaels et al. |
| 8,454,265 B2 | 6/2013 | Carroll |
| 8,510,997 B2 | 8/2013 | Nakamori et al. |
| 8,534,945 B2 | 9/2013 | Muhr-Sweeney |
| 2001/0014386 A1 | 8/2001 | Doppelreiter et al. |
| 2001/0014388 A1 | 8/2001 | Bastioli et al. |
| 2001/0021711 A1 | 9/2001 | Beilfuss et al. |
| 2001/0048974 A1 | 12/2001 | Cai |
| 2002/0065400 A1 | 5/2002 | Raskin et al. |
| 2002/0106504 A1 | 8/2002 | Stott |
| 2002/0115972 A1 | 8/2002 | Dabi et al. |
| 2002/0127374 A1 | 9/2002 | Spratling |
| 2002/0136862 A1 | 9/2002 | Dong et al. |
| 2002/0168503 A1 | 11/2002 | Dong et al. |
| 2002/0174500 A1 | 11/2002 | Micciche et al. |
| 2002/0192272 A1 | 12/2002 | Popp |
| 2003/0017565 A1 | 1/2003 | Echigo et al. |
| 2003/0026976 A1 | 2/2003 | Skrzyniarz et al. |
| 2003/0104135 A1 | 6/2003 | Grantham et al. |
| 2003/0104151 A1 | 6/2003 | Buono et al. |
| 2003/0106699 A1 | 6/2003 | Reiss et al. |
| 2003/0107144 A1 | 6/2003 | Lowe |
| 2003/0116748 A1 | 6/2003 | Haslim |
| 2003/0118814 A1 | 6/2003 | Workman, Jr. et al. |
| 2003/0129384 A1 | 7/2003 | Kalchbrenner |
| 2003/0134015 A1 | 7/2003 | Plaschke |
| 2003/0139712 A1 | 7/2003 | Dodge, II et al. |
| 2003/0150182 A1 | 8/2003 | Chou et al. |
| 2003/0155695 A1 | 8/2003 | Lund et al. |
| 2003/0158344 A1 | 8/2003 | Rodriques et al. |
| 2003/0165669 A1 | 9/2003 | Nowak et al. |
| 2003/0180440 A1 | 9/2003 | Elfersy et al. |
| 2003/0182895 A1 | 10/2003 | Skrzyniarz et al. |
| 2003/0183466 A1 | 10/2003 | Thayer |
| 2003/0192958 A1 | 10/2003 | Miyagi |
| 2003/0203010 A1 | 10/2003 | Wallo |
| 2003/0213168 A1 | 11/2003 | Hesse et al. |
| 2003/0216539 A1 | 11/2003 | Siclovan et al. |
| 2003/0219594 A1 | 11/2003 | Qin et al. |
| 2003/0235601 A1 | 12/2003 | Hallahan |
| 2004/0013757 A1 | 1/2004 | Huang et al. |
| 2004/0023025 A1 | 2/2004 | Magnin |
| 2004/0063367 A1 | 4/2004 | Dodge, II et al. |
| 2004/0065661 A1 | 4/2004 | Wiegner |
| 2004/0066299 A1 | 4/2004 | Hanabusa et al. |
| 2004/0071757 A1 | 4/2004 | Rolf |
| 2004/0074205 A1 | 4/2004 | Stache |
| 2004/0096624 A1 | 5/2004 | Albright |
| 2004/0107484 A1 | 6/2004 | Butter-Jentsch et al. |
| 2004/0108238 A1 | 6/2004 | Maresh |
| 2004/0109853 A1 | 6/2004 | McDaniel |
| 2004/0110657 A1 | 6/2004 | Strothoff |
| 2004/0115354 A1 | 6/2004 | Filippou et al. |
| 2004/0115460 A1 | 6/2004 | Torgovnikov et al. |
| 2004/0116545 A1 | 6/2004 | Jakobstroer et al. |
| 2004/0181180 A1 | 9/2004 | Wood |
| 2004/0234701 A1 | 11/2004 | Caton |
| 2004/0241392 A1 | 12/2004 | Sorrentino |
| 2004/0241540 A1 | 12/2004 | Tsutsumi et al. |
| 2004/0247917 A1 | 12/2004 | Mendes |
| 2004/0253166 A1 | 12/2004 | Kruesi |
| 2004/0253428 A1 | 12/2004 | Wang et al. |
| 2004/0255538 A1 | 12/2004 | Ruhdorfer |
| 2005/0004285 A1 | 1/2005 | Delabroye et al. |
| 2005/0016673 A1 | 1/2005 | Krebs et al. |
| 2005/0038182 A1 | 2/2005 | Hermescec et al. |
| 2005/0042168 A1 | 2/2005 | Kruesi |
| 2005/0042436 A1 | 2/2005 | Glorioso et al. |
| 2005/0051921 A1 | 3/2005 | Winterowd et al. |
| 2005/0054807 A1 | 3/2005 | Winterowd |
| 2005/0112166 A1 | 5/2005 | Hallahan |
| 2005/0118911 A1 | 6/2005 | Nun et al. |
| 2005/0137252 A1 | 6/2005 | Scialdone |
| 2005/0155691 A1 | 7/2005 | Nowak et al. |
| 2005/0158561 A1 | 7/2005 | Wang et al. |
| 2005/0166531 A1 | 8/2005 | McDonald |
| 2005/0169947 A1 | 8/2005 | Korte et al. |
| 2005/0196628 A1 | 9/2005 | Lloyd et al. |
| 2005/0217537 A1 | 10/2005 | Knipe |
| 2005/0230073 A1 | 10/2005 | Hesse et al. |
| 2005/0244521 A1 | 11/2005 | Strickland et al. |
| 2005/0244626 A1 | 11/2005 | Leslie |
| 2005/0250900 A1 | 11/2005 | Stofko |
| 2005/0260369 A1 | 11/2005 | Graf et al. |
| 2005/0263456 A1 | 12/2005 | Cooper et al. |
| 2005/0271599 A1 | 12/2005 | Matthews et al. |
| 2006/0030631 A1 | 2/2006 | Shah et al. |
| 2006/0054290 A1 | 3/2006 | Call |
| 2006/0057300 A1 | 3/2006 | Cui et al. |
| 2006/0061002 A1 | 3/2006 | Huang et al. |
| 2006/0088386 A1 | 4/2006 | Ellis |
| 2006/0100412 A1 | 5/2006 | Schmidt et al. |
| 2006/0110541 A1 | 5/2006 | Russell et al. |
| 2006/0110542 A1 | 5/2006 | Dietz et al. |
| 2006/0113044 A1 | 6/2006 | Virtanen et al. |
| 2006/0124303 A1 | 6/2006 | Nguyen et al. |
| 2006/0128886 A1 | 6/2006 | Winterowd |
| 2006/0142175 A1 | 6/2006 | Haiss et al. |
| 2006/0155013 A1 | 7/2006 | Bumm et al. |
| 2006/0185087 A1 | 8/2006 | Coppens et al. |
| 2006/0188650 A1 | 8/2006 | Sauer |
| 2006/0230707 A1 | 10/2006 | Roe et al. |

(56) References Cited

U.S. PATENT DOCUMENTS

| | | |
|---|---|---|
| 2006/0240079 A1 | 10/2006 | Hallahan et al. |
| 2006/0240243 A1 | 10/2006 | Leslie |
| 2006/0249715 A1 | 11/2006 | Salyer et al. |
| 2006/0254976 A1 | 11/2006 | Cooper |
| 2006/0273477 A1 | 12/2006 | Watt |
| 2006/0293418 A1 | 12/2006 | Matuana et al. |
| 2007/0020189 A1 | 1/2007 | Maynard |
| 2007/0020476 A1* | 1/2007 | Kintzley ............... B27N 3/002 428/537.1 |
| 2007/0031919 A1 | 2/2007 | Dunson, Jr. et al. |
| 2007/0105977 A1 | 5/2007 | Gabriel et al. |
| 2007/0110984 A1 | 5/2007 | Reedy |
| 2007/0114621 A1 | 5/2007 | Wisnudel et al. |
| 2007/0122558 A1 | 5/2007 | Gibiat et al. |
| 2007/0128428 A1 | 6/2007 | Moriya et al. |
| 2007/0149409 A1 | 6/2007 | Burnet et al. |
| 2007/0154639 A1 | 7/2007 | Malinger et al. |
| 2007/0169626 A1 | 7/2007 | Sullivan |
| 2007/0193164 A1 | 8/2007 | Gilbert |
| 2007/0193175 A1 | 8/2007 | Hao |
| 2007/0196170 A1 | 8/2007 | McDonald et al. |
| 2007/0204558 A1 | 9/2007 | Carroll |
| 2007/0207222 A1 | 9/2007 | Yu et al. |
| 2007/0227087 A1 | 10/2007 | Nasr et al. |
| 2007/0249805 A1 | 10/2007 | Ittel et al. |
| 2007/0259168 A1 | 11/2007 | Reedy |
| 2007/0261361 A1 | 11/2007 | McDonald |
| 2007/0275101 A1 | 11/2007 | Lu et al. |
| 2007/0298006 A1 | 12/2007 | Tomalia et al. |
| 2008/0029926 A1 | 2/2008 | Steinwender et al. |
| 2008/0053922 A1 | 3/2008 | Honsinger, Jr. et al. |
| 2008/0081071 A1 | 4/2008 | Sanghvi et al. |
| 2008/0096004 A1 | 4/2008 | Crostic |
| 2008/0103281 A1 | 5/2008 | Harvey et al. |
| 2008/0105195 A1 | 5/2008 | Vaerewyck |
| 2008/0171150 A1 | 7/2008 | Hesse et al. |
| 2008/0171231 A1 | 7/2008 | Lopez et al. |
| 2008/0199682 A1 | 8/2008 | Browne |
| 2008/0207481 A1 | 8/2008 | Meine et al. |
| 2010/0297458 A1 | 11/2010 | Khemani et al. |
| 2011/0305841 A1* | 12/2011 | Stark ............... A01N 25/30 427/351 |
| 2012/0276302 A1 | 11/2012 | Thomas et al. |

FOREIGN PATENT DOCUMENTS

| | | | |
|---|---|---|---|
| CA | 1 160 386 | 1/1984 | |
| CA | 2 101 833 | 8/1993 | |
| CA | 2 125 316 | 6/1994 | |
| CA | 2 201 171 | 8/1995 | |
| CA | 2 229 005 | 5/1997 | |
| CA | 2 318 633 | 9/2000 | |
| CA | 2 364 509 A1 | 9/2000 | |
| CA | 2 395 455 A1 | 6/2001 | |
| CA | 2 472 610 A1 | 7/2003 | |
| CA | 2 436 644 A1 | 2/2004 | |
| CA | 2 538 363 A1 | 4/2005 | |
| CA | 2 240 180 | 1/2008 | |
| CA | 2 311 614 C | 5/2009 | |
| CA | 2 259 739 A1 | 3/2010 | |
| DE | 19704365 A1 | 11/1997 | |
| DE | 19839292 A1 | 3/2000 | |
| DE | 10061059 A1 | 6/2001 | |
| DE | 10233179 A1 * | 2/2004 | ............ C09B 69/102 |
| DE | 102005062608 A1 | 7/2007 | |
| EP | 0 230 301 A3 | 1/1987 | |
| EP | 0 337 474 A2 | 10/1989 | |
| EP | 0 567 440 A2 | 10/1993 | |
| EP | 0 841 100 A1 | 5/1998 | |
| EP | 0 867 770 A1 | 9/1998 | |
| EP | 0 949 296 A1 | 10/1999 | |
| EP | 1 205 521 A1 | 5/2002 | |
| RU | 2067928 C1 | 10/1996 | |
| WO | WO 1981/00267 | 2/1981 | |
| WO | WO 1985/001294 A1 | 3/1985 | |
| WO | WO 1986/007013 A1 | 12/1986 | |
| WO | WO 1991/013112 A1 | 9/1991 | |
| WO | WO 1992/011322 A2 | 7/1992 | |
| WO | WO 1992/021514 | 12/1992 | |
| WO | WO 1993/09741 | 5/1993 | |
| WO | WO 1998/47953 A1 | 10/1998 | |
| WO | WO 1999/001516 A1 | 1/1999 | |
| WO | WO 1999/003512 A2 | 1/1999 | |
| WO | WO 1999/024498 A2 | 5/1999 | |
| WO | WO 1999/032534 A1 | 7/1999 | |
| WO | WO 1999/061539 A1 | 12/1999 | |
| WO | WO 2000/05123 A2 | 2/2000 | |
| WO | WO 2000/005185 A1 | 2/2000 | |
| WO | WO 2000/027967 A1 | 5/2000 | |
| WO | WO 2000/052082 A2 | 9/2000 | |
| WO | WO 2001/005919 A2 | 1/2001 | |
| WO | WO 2001/046327 A2 | 6/2001 | |
| WO | WO 2001/056756 A1 | 8/2001 | |
| WO | WO 2001/096516 A1 | 12/2001 | |
| WO | WO 2002/029179 A1 | 4/2002 | |
| WO | WO 2002/100233 A1 | 12/2002 | |
| WO | WO 2003/013843 A1 | 2/2003 | |
| WO | WO 2003/037531 A1 | 5/2003 | |
| WO | WO 2003/056096 A1 | 7/2003 | |
| WO | WO 2003/074572 A1 | 9/2003 | |
| WO | WO 2004/037871 A1 | 5/2004 | |
| WO | WO 2004/085102 A2 | 10/2004 | |
| WO | WO 2005/037545 A2 | 4/2005 | |
| WO | WO 2006/049479 A1 | 5/2006 | |
| WO | WO 2006/057558 A1 | 6/2006 | |
| WO | WO 2013/009286 A1 | 1/2013 | |

OTHER PUBLICATIONS

Attwood, D. and Florence, A.T., *Surfactant Systems Their chemistry, pharmacy and biology* (1983), (cover page, publication page, and pp. 1-11).

Materials Research Society Symposium Proceedings vol. 124, Microwave Processing of Materials held Apr. 5-8, 1988, *Microwave Processing of Polymers and Biomass Materials* by George et al. (cover page, publication page, pp. 189-194).

Materials Research Society Symposium Proceedings vol. 430, Microwave Processing of Materials V, Symposium held Apr. 8-12, 1996, *Monitoring Resin Cure of Medium Density Fiberboard using Dielectric Sensors* by R.J. King and R.W. Rice (cover page, publication page, table of contents p. v, and pp. 601-605).

Materials Research Society Symposium Proceedings, vol. 124, Microwave Processing of Materials, Symposium held Apr. 5-8, 1998, *Microwave Processing at Ontario Hydro Research Division* by S.J. Oda and I.S. Balbaa (cover page, publication page, table of contents p. v, and pp. 302-309).

MSDS, Shaklee Corporation, Get Clean™ Basic H2™, May 21, 2007, 3 pages.

Przewloka et al., *Assessment of commercial low viscosity resins as binders in the wood composite material*, Vintorg, Holz Roh Werkst, (2007) vol. 65 (pp. 209-214).

Rafalski et al., *Small waves against great destroyers, microorganism control in wood using microwave techniques and microwave technology*, Bautenschutz + Bausanierung, (2004) vol. 26, Issue 6 (pp. 37-38, 40-41).

Saito et al., *Microwave-enhanced release of formaldehyde from plywood*, Holzforschung (2004) vol. 58 (pp. 548-551).

Shutov, G.M., *Modification of Wood with Synthetic Resins using Energy of a High-Frequency Electromagnetic Field*, Zesz. Probl. Postepow Nauk Roln. No. 231 (1980) 39-53; English abstract (1 page).

Torgovnikov, G. and Vinden, P., *New microwave Technology and Equipment for Wood Modification*, 2004 AIChE Annual Meeting (2004), 3 pages.

\* cited by examiner

PRESERVATION OF CELLULOSIC MATERIALS, COMPOSITIONS AND METHODS THEREOF

CROSS-REFERENCE

This application claims priority to Provisional Patent Application Ser. No. 61/503,091, filed Jun. 30, 2011, which application is incorporated herein by reference in its entirety.

FIELD

The disclosure relates to compositions for preservation of cellulosic materials and methods for using compositions for preservation of cellulosic materials at low pressures or atmospheric pressures.

BACKGROUND

Treatment of cellulosic materials to extend their serviceable life (preservation) has many applications. Treated wood is used in fence posts, utility poles, residential and commercial decking, utility poles, railroad ties and the like.

Most methods used to treat wood are often energy and labor intensive. Presently, treatment of sapwood can require subjecting wood to a vacuum, followed by high pressure to impregnate the wood with treatment compositions. Pressures in the range of 50-250 psig can be used for preservation of wood. Typically, the use of high pressure for wood treatment requires costly pressure containment vessels, controllers and pumps. Associated maintenance costs of those pressure containment vessels and pumps can be high to assure that the pressure vessels maintain integrity (e.g. do not leak) and thus can hold pressure/vacuum. Furthermore, energy requirements of pumps for evacuation and pressurizing the pressure vessels can be high and costly. U.S. Pat. No. 3,968,276 (Allen), U.S. Pat. No. 4,399,195 (Allen) and U.S. Pat. No. 4,433,031 (Allen) disclose wood treatment compositions and methods, and are incorporated herein by reference in their entirety. Currently, most wood treatment procedures use toxic chemicals and preservatives that can have a serious impact on the environment over the lifetime of the treated wood, and during disposal of the treated wood at the end of its serviceable life. These treatment procedures may also be ill-suited to treat other cellulosic materials, such as cardboard or paperboard or mulch.

It is against this background that this disclosure is made.

SUMMARY

Surprisingly, the disclosed compositions and methods allow for improved treatment of cellulosic material. Accordingly, some aspects of the disclosure relate to a method of preserving cellulosic material by contacting the material with a composition, and allowing the composition to soak into the wood over a period of time and cure. The wood preserving composition is a solution of pre-polymer and an optional nonionic surfactant.

The disclosed compositions and methods advantageously allow for reduced energy expenditures for treatment of wood, simpler, less expensive equipment for wood preservation, or environmentally safe, non-toxic alternatives to current technologies for wood preservation.

DETAILED DESCRIPTION

As used herein, the following definitions define the stated term:

A "pre-polymer" is an organic chemical that can be polymerized to produce a polymer. The pre-polymer is typically soluble in water or another suitable solvent, e.g., ethanol or methanol.

A "blend" or "resin blend" implies a mixture of pre-polymers that has a wide range of molecular weights (m) within one pre-polymer composition. Though not limiting, an example of a resin blend is a composition of pre-polymers with molecular weights from about 180 to about 10,000. Another example of a resin blend is a composition of pre-polymers with molecular weights from about 180 to about 10,000 with very little, if any, formaldehyde.

The term "impregnation" refers to a state in which the specific material being treated with a solution (i.e. composition) reaches a refusal point whereby the material cannot accept or absorb any further solution under the given process conditions and composition parameters. The term is used interchangeably with "saturation" in this disclosure.

The term "curing" refers to polymerization or crosslinking of a pre-polymer. The pre-polymers comprised in the composition contain reactive sites that can react/crosslink (i.e. polymerize) with another pre-polymer or with other reactive sites, such as reactive sites on cellulose, hemicellulose, or lignin in the cellulosic material. In some cases, curing can be a combination of polymerization with other like pre-polymers and polymerization with reactive sites of other types of molecules. Curing (or polymerization) can be induced by a combination of time and temperature in a temperature dependent polymerization system.

The term "low pressure" refers to process pressures between about atmospheric pressure and about 24 psig.

The term "preservative" refers to any material applied to wood which can act as an insect repellant, an insecticide, a microorganism repellant, a rot retardant, a biocidal agent, a fire retardant, a fire-proofing agent or combinations thereof.

The terms "environmentally safe" and "non-toxic" are used to describe compositions that are exempt from current EPA regulations for wood preservatives, because the compositions contain no toxic ingredients or chemicals.

Methods of Preserving Cellulosic Materials

Cellulosic materials, such as wood, wood veneer, particle board, fiberboard, cardboard, paperboard and other similar materials and structures may be treated to modify their properties for various uses and to extend their serviceable life. Such materials in their natural state are susceptible to damage by natural forces (e.g. wind, rain, frost, heat, sun light, ozone), or by animals (e.g. woodpeckers), insects (e.g. termites) and microbes (e.g. fungi such as wood rot). Damaged structures pose a safety risk and can be costly to repair or replace. Woods that can be treated range from soft woods, such as for example pine, to hard woods such as for example oak or maple.

According to an embodiment of the present disclosure, cellulosic materials may be treated by bringing them into contact with a composition comprising a pre-polymer and optionally a surfactant, and curing. The constituents of the composition, as well as the application and curing methods, can be modified depending on the desired result. For example, different pre-polymers and application methods can be used to achieve a hard and durable wood product to be used in utility posts or railroad ties, or to achieve a fire-retardant fiberboard for use in home construction, or to achieve a weather resistant decking material.

Because compositions and methods of the present disclosure allow for treatment of cellulosic materials in ambient temperature and at or near ambient pressure, energy expenditures of the treatment are greatly reduced when compared with vacuum/pressure treatment methods presently used in the wood preservation industry. Certain embodiments of the present disclosure also require simpler, less expensive equipment in that vacuum and pressure equipment can be eliminated and replaced, for example, by fluid containing vessels and/or spray equipment.

Preserving cellulosic materials, including wood and green wood, with pre-polymer compositions of the present disclosure also imparts dimensional stability by chemically binding the fibers of the material together and by reducing hygroscopicity and giving protection from weathering by rendering materials resistant to rain, UV rays and ozone. In some embodiments preserving materials with pre-polymer compositions increases hardness, compression strength and modulus. Wooden materials will also become resistant to splitting and splintering. The treated material can additionally have increased fastener holding power, such as, for example nails, screws, railroad spikes and other fasteners.

Only a minor decrease in tensile strength can be observed in some species of wood. For example, the modulus of elasticity of phenol-formaldehyde treated wood increases from about 35 to about 40%. The modulus of rupture of phenol-formaldehyde treated wood increases from about 27 to about 43%, with a tensile strength decrease of only about 10%.

The capability to improve structural and other qualities of materials by the use of embodiments of the present disclosure allows for the use of more economical materials in applications that traditionally would require materials that are ordinarily harder, more durable and more costly. For example, treated softwoods (such as pine) can be used where typically hardwood would be preferred, or treated fiberboard or particleboard can be used where typically plywood would be preferred.

The compositions and methods of the present disclosure are particularly suited for treating wood knots. Over time, as wood dries, knots separate from the rest of the wood, leaving an undesirable hole. The compositions of the present disclosure bond the knot to the rest of the wood so it does not fall out. Therefore wood with knots can now be used where it may have been discarded in the past, increasing the profitability of sawmill operations.

According to an exemplary embodiment, the present compositions have been found to advantageously discourage woodpecker nesting in utility poles by making the exterior of a wood surface, especially of utility poles, resistant to damage from woodpeckers. Woodpeckers nest in wooden utility poles by drilling horizontally into the interior of the pole, and then drilling vertically to create a nest. The vertical nest makes the pole susceptible to damage from weather and strong winds and, if damaged, can cause an outage in services. Treatment of the utility pole to make the exterior stronger makes it less likely that woodpeckers will be able to drill into the interior. According to an embodiment, the treatment may also make the interior of the pole harder, thus deterring woodpeckers, and more rot-resistant, causing it to be better able to withstand other environmental damage.

According to other embodiments, the present compositions have also been found to retard fire. The present compositions may also provide UV and ozone protection to cellulosic structures.

The Composition

The compositions and methods for preservation of materials of the present disclosure provide environmentally safe, non-toxic alternatives to current technologies, which are environmentally harmful.

The composition for treatment of cellulosic materials may comprise a suitable pre-polymer (or pre-polymers), a solvent (or solvents), and optionally a surfactant or other additives that may aid in the application or curing of the composition, or may provide desirable qualities to the end product. The composition may also comprise pigmentation, enabling its use in lieu of paint to treat surfaces. By varying the characteristics of the pre-polymer, it is possible to tailor the preservative composition to particular applications. For example, the modulus of elasticity, modulus of rupture, hardness and other qualities of the treated cellulosic product can be modified by the choice of pre-polymer used, the amount of pre-polymer and the pH of the composition.

The pre-polymer can be chosen such that it is soluble in a suitable, non-toxic solvent. From an economic perspective, and because water can be easily accessible at treatment sites, according to an exemplary embodiment, the pre-polymer can be water soluble. The pre-polymer may also be soluble in ethanol or methanol. According to an exemplary embodiment, the composition comprises water. According to another embodiment, the composition may comprise alcohol (e.g. ethanol or methanol), or a combination of alcohol and water. Premature curing of the composition (i.e. curing before the composition has been contacted with the material to be treated) may be avoided by including ethanol or methanol as a solvent, by avoiding subjecting the pre-polymer solution or the composition to increased temperatures for extended periods of time, and storing the composition in a closed container. In some embodiments, a shelf life of over 2 years may be obtained.

Pre-polymers of different sizes and molecular weights not only impart different qualities on the end product, but are capable of penetrating the cellulosic material to varying degrees. The molecular weight distribution of the pre-polymer can be adjusted such that when the pre-polymer solution contacts the material to be treated, the pre-polymer can impregnate the material to an effective level to provide desired preservation qualities, or can be used to preferentially treat the outer surface of the material and provide a thick protective crust on the surface. For example, the higher molecular weight fractions (i.e. about 500 to 900 or higher) will generally form a crust or "skin" on the outer surface of the material, while the lower molecular weight fractions (i.e. 180 to about 500) will preferentially penetrate into the various interior layers of the material, optionally penetrating all the way to the core, increasing hardness, resistance to compression, and the like. Crust hardness and toughness can vary based on the type of pre-polymer chosen. Generally, pre-polymer compositions with low weight-average molecular weight and therefore low viscosity can be advantageous for ease of use.

Wooden materials contain cells that comprise a wall (i.e. cell wall) composed of cellulose and lignin, and a cavity (i.e. lumen). According to an embodiment, pre-polymers of the composition may penetrate the wooden material and enter into the inside of the cell cavities. During polymerization the pre-polymers may polymerize and remain within the cell cavity and may become part of the permanent structure of the material. The pre-polymers may also bind with reactive sites of the lignin and cellulose. According to another embodiment, pre-polymers of the composition may penetrate cellulosic materials that no longer contain cells, and during polymerization bind with other pre-polymers and reactive sites of the cellulose. Penetration into wood or other cellulosic materials may be facilitated by altering the pre-polymer (smaller pre-polymers are more capable of penetrating into the materials) and by altering the pressure used during treatment.

The use of a composition that comprises a blend of pre-polymers with molecular weights over a wide range, from very low (i.e. 180) to very high (i.e. 10,000) allows for preferential treatment or protection of a structure. By pressure-treating or soaking material with the resin blend, different parts of the material are coated with polymers having different molecular weight. Therefore, by carefully controlling the molecular weight distribution of the resin blend, it is possible to provide tailor-made preservative compositions for specific applications. According to exemplary embodiments, it may be advantageous to employ a blend of pre-polymers to achieve specific outcomes, such as for example, but not limited to, preserving green lumber, or for preferential coating of surfaces and strengthening of the core for certain applications, such as utility poles. Some exemplary blends include a first pre-polymer with a molecular weight from about 5,000 to about 10,000 and a second pre-polymer with a molecular weight from about 180 to about 5,000, or a first pre-polymer with a molecular weight from about 180 to about 1,000 and a second pre-polymer with a molecular weight from about 5,000 to about 8,000.

In some embodiments the pre-polymer can be a condensation pre-polymer. Examples of condensation pre-polymers in accordance with the present disclosure include, but are not limited to, urea derivatives, melamine derivatives, phenol derivatives, and combinations thereof. Specific exemplary pre-polymer resins that can be used include, but are not limited to urea-formaldehyde, urea-melamine-formaldehyde, urea-furfural, phenol-formaldehyde or mixtures thereof. According to some embodiments, the composition may comprise a formaldehyde-free pre-polymer, such as methylene diphenyl isocyanate (MDI) or polyvinyl acetate (PVA).

According to exemplary embodiments, the pre-polymer comprises a phenol-formaldehyde pre-polymer with a weight-average molecular weight ($MW_w$) in the range of from about 180 to about 10,000. In other embodiments the weight-average molecular weight ($MW_w$) can be less than about 10,000, less than about 8000, less than about 5000, less than about 4000, less than about 2000, less than about 1000, less than about 900, about 400 to about 900, about 500 to about 900, about 600 to about 900, about 700 to about 900, or about 800 to about 900.

In some other embodiments, the pre-polymer is a resin blend or mixture of phenol-formaldehyde pre-polymers having different molecular weights ranging from a molecular weight of about 180 to a molecular weight of about 10,000 in a single composition.

In some embodiments, the composition contains very low concentrations of formaldehyde, i.e. no greater than about 0.2% or less than 0.1%, and more preferably less than 0.07%, or most preferably less than 0.05%. In some embodiments, the composition can be substantially free of formaldehyde. According to some embodiments, compositions for treatment of products for consumer markets can be free of formaldehyde. For example, products for home construction (structural components, trims, shingles, fence posts, floor boards, etc.) or construction of motor homes, mobile homes or log homes may be treated with formaldehyde-free compositions. A composition for use at the home may also be provided, for example, for treating outside structures, such as decks, fences, picnic tables or playground equipment.

Compositions for preservation of cellulosic materials of the present disclosure can contain up to about 50 wt % of pre-polymer, from about 2.0 wt % to about 50 wt % pre-polymer, or from about 2.0 wt % to about 20 wt % pre-polymer. In other embodiments in accordance with the present disclosure, compositions for preservation of cellulosic materials can contain about 50 wt %, about 40 wt %, about 30 wt %, about 25 wt %, about 20 wt %, about 15 wt %, about 12 wt %, about 10 wt %, about 8 wt %, about 6 wt %, about 5 wt %, about 4 wt % or even about 3 wt % pre-polymer, depending upon the density of wood being treated, the physical and chemical characteristics of the pre-polymer being used, the desired impregnation level of the preservative, and the desired qualities of the end product.

The pH of the composition can be adjusted to facilitate the polymerization reaction. For example, the pH of the composition can be alkaline. According to an exemplary embodiment, the pH of the composition may be adjusted to an alkaline pH. According to a preferred embodiment, the pH of the composition may be adjusted to from about 7.5 to about 13. According to a most preferred embodiment, the pH of the composition may be adjusted to about 12.5

Nonionic Surfactants

The composition for treatment of cellulosic materials can optionally include nonionic surfactants. Suitable nonionic surfactants for use in accordance with the present disclosure include alkoxylated surfactants and alkyl polyglycosides.

Nonionic surfactants employed in compositions of the present disclosure can be at concentrations higher than those conventionally employed as surfactants. For example, in some embodiments, concentrated compositions can include up to about 2.0 wt. % of nonionic surfactants. In some embodiments, concentrated compositions can include from about 0.01 wt % to about 1.0 wt % of nonionic surfactants. In other embodiments, nonionic surfactant mixtures can include up to about 0.9 wt %, about 0.7 wt %, about 0.5 wt %, about 0.3 wt %, about 0.1 wt %, about 0.08 wt %, about 0.06 wt %, about 0.04 wt %, or about 0.02 wt % of the composition. According to alternative embodiments, the composition can be substantially free of nonionic surfactants. In other embodiments, the composition can be free of nonionic surfactants.

Suitable alkoxylated surfactants for use in the composition include ethylene oxide/propylene oxide (EO/PO) copolymers, capped EO/PO copolymers, alcohol alkoxylates, capped alcohol alkoxylates, mixtures thereof, or the like. Examples of suitable alkoxylated surfactants include EO/PO block copolymers, such as poloxamers (e.g. Pluronic®, available from BASF, Florham Park, N.J.) and reverse poloxamer surfactants; alcohol alkoxylates such as "DEHYPON LS 54" and "DEHYPON LS 36" (available from BASF, Florham Park, N.J.); and capped alcohol alkoxylates, such as "PLURAFAC LF-221" (available from BASF, Florham Park, N.J.) and "TEGOTENS EC 11" (available from Evonik Industries AG, Essen, Germany); and mixtures thereof, or the like.

Ethoxylated alcohols useful in some embodiments of the present disclosure include C12-C16 ethoxylated alcohols, "ALFONIC 1216-1.3" and "ALFONIC 1216-22" (available from Sasol North America Inc., Houston, Tex.), "BEROL 175" (available from AkzoNobel N.V., Amsterdam, the Netherlands), "DEHYDROL LSS 5.5" (available from Melrose Chemicals, Ltd., Lachine, QC, Canada), "GENAPOL 24L50", "GENAPOL 26L3", "GENAPOL 26L80", "GENAPOL LA 060", "GENAPOL UD 030S" (available from Clariant International, Ltd, Charlotte, N.C.), "MERPOL HCS" (available from Stepan Company, Northfield, Ill.), "NEONOL P 12-16-3" (available from Okachim, Samara, Russia), "ETHONIC 1214-2", "ETHONIC 1214-6.5", "GENAPOL 24/50", "ALEX 12.0", "ALEX 4.0", and "ALEX 6.0."

In some embodiments of the present disclosure, oligomeric alkylpolyglycosides such as D-glucopyranose, $C_{10}$-$C_{16}$ alkyl glycosides and oligomeric D-glucopyranose, decyl octyl glycosides (CAS—110615-47-9), linear alcohol alkoxylates (CAS—37251-67-5; 68551-12-2), and pareth 25-7 (CAS—68131-39-5), or mixtures thereof, can be used in surfactant mixtures of the compositions.

Examples of pareth 25-7 can include "ALFONIC 1012-40", "LIALET 125/5", "MARLIPAL 025/70" (available from Sasol North America Inc., Houston, Tex.), "ANAPOE C13E8" (available from Affymetrix Inc., Santa Clara, Calif.), "BIO-SOFT EN 600" (available from Stepan Company, Northfield, Ill.), "NEODOL 25-12", "NEODOL 25-9", "DOBANOL 25-7", "DOBANOX 25-7" (available from Shell Chemical LP, Houston, Tex.), "EMPILAN KCL 9" (available from Huntsman Corporation, The Woodlands, Tex.), "GENAPOL 26L45", "GENAPOL LA 050" (available from Clariant International, Ltd, Charlotte, N.C.), "IMBENTIN C 125/094" (available from Kolb Distribution, Ltd, Hedingen, Switzerland), "MULSIFAN RT 203/80" (available from Zschimmer & Schwarz GmbH, Lahnstein, Germany), "EMERSIST 7232", "ADEKATOL SO 160", "AE 25-15A", "AEO 40", "AEO 9", "C12-15 PARETH 3", "C12-15 PARETH-9", and "NEONOL P 1215-3."

Additionally, examples of linear alcohol alkoxylates can include 2-methyl oxirane monodecyl ether, methyl oxirane monodecyl ether, EO/PO copolymer monodecyl ether, polyethylene/polypropylene glycol monodecyl ether, "BIODAC 11009", "BIODAC OP 1" (available from Sasol North America Inc., Houston, Tex.), "EMALEX DAPE 0203", "EMALEX DAPE 0230" (available from Nihon Emulsion Co., Ltd., Tokyo, Japan), "ETHOX 1437", "ETHOX 1449" (available from Ethox Chemicals, LLC, Greenville, S.C.), "EUSAPON LD 6031", "LUTENSOL XL 60" (available from BASF, Florham Park, N.J.), "FINESURF ELP 1608B" (available from Aoki Oil Industrial Co., Ltd., Osaka, Japan), "NOIGEN XL 60" (available from Dai-Ichi Karkaria Ltd., Mumbai, India) and "PEGNOL D 218."

Other Additives

The quality of the treated end product may be engineered to best suit particular uses by incorporating other additives into the composition. For example, pigments or dyes may be added to compositions that are used to treat construction elements, such as floor boards, trim, siding, shingles, etc. Fluorescent dyes may be added to compositions that are used to treat structures that benefit from high visibility, for example structures used at road construction sites.

The quality of the end product may also be altered by using Atom Transfer Radical Polymerization (ATRP), wherein a transition-metal (e.g. copper) based catalyst is added into the composition. The metal catalyst, together with an initiator (e.g. an alkyl halide), partake in the polymerization reaction, and can be used to direct the reaction toward particular polymeric structures with few side reactions. The choice of pre-polymer may also be varied to optimally facilitate the ATRP reaction. For example, a pre-polymer with a phenyl or acrylate group may be chosen.

According to exemplary embodiments, other catalysts may be added to facilitate polymerization.

To further increase resistance to fire, specific fire retardant chemicals may be added to the composition in suitable amounts. Application of the Composition to Materials The composition can be brought into contact with the material to be treated using many different methods. The composition can, for example, be applied by submersing the material in the composition or by spraying, dripping, curtain-coating, brushing, atomizing, sonicating, applying with a reciprocating arm (similar in action to a windshield wiper), or wiping the composition onto the material or by combinations thereof. While submersion allows for the complete and thorough treatment of the material, some of the other methods are more applicable to treating existing structures, such as fence posts and utility posts.

According to some embodiments, it may be desirable to provide for conditions that allow at least some pre-polymers to penetrate the surface of the material and reach the inner parts of the material. It may be desirable to impregnate the material (e.g. by submersion) such that no more pre-polymer solution can be absorbed. In an embodiment of the present disclosure, the compositions can be charged to a tank and the material to be treated can be submerged in the composition in the tank to allow intimate contact of the material with the composition treatment bath and absorption of the pre-polymer solution. The treatment bath can be stirred to ensure contact of the composition with the material. Alternatively, the material to be treated can be submerged in the bath without stirring. According to alternative embodiments, the material to be treated can be partially submerged into the composition and then rotated such that all surfaces of the material are contacted with the composition. Alternatively, only one or some of the sides of a structure can be contacted with the composition. The impregnation or saturation time varies based on the permeability of the material and can occur in as little as ten seconds, or may take several minutes.

Materials can be treated by submersion at atmospheric pressure, but in order to speed the penetration of the pre-polymers into the material, the material can be subjected to pressure, for example, but not limited to pressures between about atmospheric and about 24 psig. In other embodiments, the treated wood can be subjected to pressures between about atmospheric and about 22 psig, between about atmospheric and about 20 psig, between about atmospheric and about 18 psig, between about atmospheric and about 16 psig, between about atmospheric and about 14 psig, between about atmospheric and about 12 psig, between about atmospheric and about 10 psig, between about atmospheric and about 8 psig, between about atmospheric and about 7 psig, between about atmospheric and about 6 psig, between about atmospheric and about 5 psig, between about atmospheric and about 4 psig, between about atmospheric and about 3 psig, between about atmospheric and about 2 psig or even in some cases between about atmospheric and about 1 psig.

Other methods of contacting wood to be preserved with the compositions can include, but are not limited to, contacting only a portion of the material to be treated with the composition. In one embodiment, such contact with portions of the wood can include dipping one or both ends of a utility pole or fence post vertically into a bath of the composition. This method can preferentially treat and preserve the portion of the utility pole or fence post that would be buried and in contact with the ground. Protecting the ends of a long pole with a "crust" may also be achieved by brush application. Application by brush may be preferable in situations where equipment (e.g. vacuum/pressurized treatment systems) is horizontally disposed and where dipping the end of a very long post or telephone pole (e.g. 10, 30 or 100 feet long) would require major modifications to the horizontally disposed systems.

Multiple subsequent instances of treatment of the same surface are possible. For example, a surface that has already been treated with the composition of the present disclosure once can be treated again either with the same composition or a different composition of the present disclosure, for example one with pigmentation. Materials treated with the composition of the present disclosure can also subsequently be sanded, painted and stained using conventional materials and methods.

Curing

Material that has been contacted with the composition can be cured by a combination of time and temperature. The curing conditions may be optimized for the particular pre-polymer and thickness/size and make-up of the material being treated. For example, a 6 inch×6 inch wooden fence post would take more time to cure than a 1 inch×6 inch board. This is due to the fact that the fence post is thicker than the board and can absorb more pre-polymer, requiring a longer time and/or higher temperature to cure. The porosity of the material may also impact the cure time, as the material may have absorbed more or less pre-polymer during the application of the composition. The cure time can also be dependent upon the original water content of the material before contact with the pre-polymer mixture.

According to an embodiment, material that has been contacted with the composition can be cured at ambient temperature or at higher than ambient temperature. According to an exemplary embodiment, the material may be heated to an elevated temperature, for example 110° F. (about 43° C.) to about 140° F. (about 60° C.). The material may be heated by subjecting it to steam or by heating in an oven. In some instances, the material can be partially cured using heat (e.g. steam or oven), and the remaining uncured material (e.g. the core) can be allowed to cure over a length of time (e.g. days or months) in use at ambient temperature of about 72° F. (about 22° C.) or greater. The material can also be cured using wave energy such as microwaves or infrared waves.

According to an embodiment, during curing the pre-polymer crosslinks with other pre-polymers. For example, but not meant to be limiting, a phenol formaldehyde pre-polymer can form a phenolic polymer. In other embodiments, curing can cause polymerization of the pre-polymer with reactive sites on the cellulosic structure of the material, which can be susceptible to reaction with the pre-polymer. Sites on the material which can be susceptible to polymerization include, but are not limited to, for example, hydroxyl groups on cellulose that can form ether linkages with the pre-polymer or with polymerized pre-polymer. In yet other embodiments in accordance with the present disclosure, curing can cause a combination of polymerization or cross-linking of the pre-polymer with other pre-polymers and of the pre-polymer with sites on the cellulosic material such as sites on the cellulose, hemi-cellulose or lignin.

It may be desirable that in some embodiments cure of the composition is only partially performed using any of the means described above. The curing can be conducted at the preservation facility such that only a portion of the pre-polymer is cured, and the remaining uncured pre-polymer will be cured at ambient temperature as the preserved material is put into use, for example, as a utility pole. This would allow for a shorter cure time at the preservation facility, thus reducing the time required for processing the preserved material, while still allowing for ultimate full curing at ambient temperature of the preserved wood over a longer period of time once in the end use environment.

EXAMPLES

In Examples 1 and 2, 8/4 white pine boards, at approximately 20% moisture content, were used to demonstrate preferential coating of different parts of a piece of wood by the resin blend composition disclosed herein.

Example 1

To 20 parts by volume of pre-polymer solution (phenol-formaldehyde pre-polymer solution with 70 wt % solids; weight-average molecular weight ($MW_w$) in the range of 400 to about 900) was added an equal amount by volume of water. The boards were loaded into a pressure tank measuring approximately 2 foot length×1 foot diameter. A sufficient amount of pre-polymer solution was added to the tank and boards to completely submerge the boards. The tank was closed and pressurized to 5 psig. After 30 minutes the tank pressure was relieved and the boards were removed and weighed. In an alternate experiment, the boards were treated by submerging in the pre-polymer solution and soaking the boards in the solution for about 30 minutes to allow impregnation or saturation. The dry weight of the pre-polymer remaining in the boards was calculated using the theoretical percent solids of the pre-polymer solution. The result dry weight for all three boards was 0.346 lbs of pre-polymer/ft$^3$ retention.

Example 2

White pine boards were treated as in Example 1 and then further treated with a dilute solution of bleach. The bleach provided a short-lived color change reaction with the polymer-treated wood that allowed visualization of the coating and impregnation of the composition into the wood.

A cross-section of a wood piece treated with a 20R resin blend shows a thick coating or crust of polymer on the surface layers of the wood and also significant uniform penetration by the composition into the interior of the wood. The pressure-treated wood shows slightly more penetration or impregnation than wood treated by soaking in the resin composition.

We claim:
1. A method for preserving cellulosic materials comprising:
 a. applying to the cellulosic material a composition so that at least one portion of the composition penetrates a surface of the cellulosic material and another portion of the composition coats the surface of the cellulosic material, wherein the composition consists of:
  from about 2.0 wt % to about 20 wt % of a mixture of a first pre-polymer having a weight-average molecular weight (MWw) of from 5,000 to about 10,000 and a second pre-polymer having a weight-average molecular weight (MWw) of less than 5,000; and
  a solvent; and
 b. curing the composition and the cellulosic material in a curing step having a duration of at least three days and comprising a curing temperature of ambient temperature and a curing pressure between atmospheric pres- sure and about 24 psig, wherein the curing temperature and curing pressure are maintained for the duration of the curing step;

wherein the cellulosic material comprises wood, and wherein curing comprises polymerization.

2. The method of claim 1, wherein the composition is applied to the material by soaking the material in the composition, or by brushing, wiping or spraying the composition on the surface of the material.

3. The method of claim 1, wherein the first pre-polymer has a weight-average molecular weight ($MW_w$) of from 5,000 to about 8,000 and the second pre-polymer has a weight-average molecular weight ($MW_w$) of from about 180 to about 1,000.

4. The method of claim 1, wherein the first and second pre-polymers are selected from the group consisting of methylene diphenyl isocyanate, polyvinyl acetate, phenol-formaldehyde, melamine-formaldehyde, urea-formaldehyde, urea-melamine-formaldehyde, urea-furfural, and mixtures thereof.

5. The method of claim 1, wherein the solvent is water or ethanol or methanol or a mixture thereof.

6. The method of claim 1, wherein at least some of the pre-polymer solution penetrates the surface of the material and wherein the pre-polymer that has penetrated the surface of the material chemically bonds to the material during curing.

7. The method of claim 1, wherein at least some of the pre-polymer solution remains on the surface of the material and wherein the pre-polymer that has remained on the surface of the material forms a protective crust on the material during curing.

8. The method of claim 1, wherein the method is capable of rendering the cellulosic material weather resistant.

9. The method of claim 1, wherein the method is capable of rendering the cellulosic material fire resistant.

10. The method of claim 1, wherein the method is capable of increasing the hardness, compression strength or modulus or combinations thereof of the cellulosic material.

11. The method of claim 1, wherein the composition has a pH of 7.5-13.

12. The method of claim 1, wherein the cellulosic material is a green wood board.

13. The method of claim 1, wherein the method is used to prepare utility poles.

* * * * *